W. J. WRIGHTON

Aug. 26, 1930. GOGGLES Re. 17,781

Original Filed May 16, 1927

Inventor

William J. Wrighton.

By Harry H. Styll.

Attorney

Reissued Aug. 26, 1930 Re. 17,781

UNITED STATES PATENT OFFICE

WILLIAM J. WRIGHTON, OF SOUTHBRIDGE, MASSACHUSETTS, ASSIGNOR TO AMERICAN OPTICAL COMPANY, OF SOUTHBRIDGE, MASSACHUSETTS, A VOLUNTARY ASSOCIATION OF MASSACHUSETTS

GOGGLES

Original No. 1,720,811, dated July 16, 1929, Serial No. 191,733, filed May 16, 1927. Application for reissue filed September 7, 1929. Serial No. 391,083.

This invention relates to improvements in ophthalmic mountings and has particular reference to an improved eye cup for a goggle or the like.

The principal object of the invention is to provide an improved eye cup having an inner and outer cup to provide indirect ventilation to the inside of the eye cup and at the same time hold and retain the resilient material which surrounds the edge of the eye cup that contacts with the face, and at the same time provide a seat for the lens.

Another object of the invention is to provide improved means for holding the face contacting member of a goggle in place.

Another object of the invention is to provide improved means for ventilating the eye cup of a goggle.

Other objects and advantages of the invention will become apparent from the following description taken in connection with the accompanying drawings, and it will be apparent that many modifications may be made in the details of construction and arrangement of parts without departing from the spirit of the invention as expressed in the accompanying claims. I, therefore, do not wish to be limited to the exact details and arrangements shown, the preferred forms only having been shown by way of illustration.

Referring to the drawings.

Figure 1:
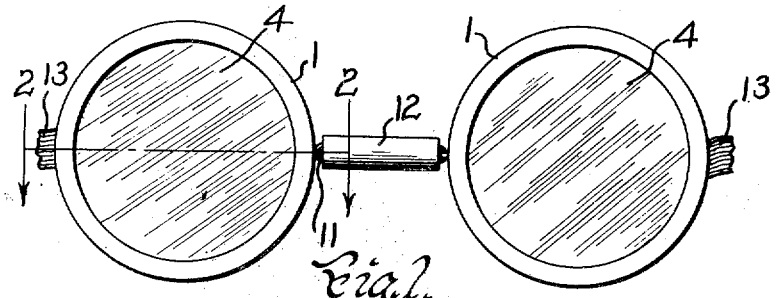
Fig. 1 shows a front view of a goggle embodying the invention.

This invention relates to the type of industrial goggle used for the protection of the eye in the arts to protect the eye from flying particles, dust, blows and hazards of a similar nature.

The invention consists primarily of an outer eye cup 1 which may be made of sheet metal, fiber or other material. The inner edge 2 of the eye cup is cut at an angle to fit the face while the outer end is provided with a shoulder or flange 3 to seat and carry a lens 4. Within the eye cup 1 is a second annular eye cup 5 which is spaced from the eye cup 1 by means of the spacing members 6. The inner end of the eye cup 5 is also cut to fit the face as in the case of the inner end of the outer cup 1. The lens 4 rests on the outer end 7 of the inner cup 5. Between the outer cup 1 and the inner cup 5 is held a rubber or other resilient facing means 8 which has a reduced flange 9 fitting between the plates of the cups 1 and 5, it being compressed between the two cups which are held together by the rivets or the like 10. This provides a simple and efficient channel for holding the flange 9 of the face contact member 8.

The two eye cups 1 are connected by a chain bridge 11 which is covered by a rubber tube 12. The eye cups are held in place on the face by means of the head band 13 attaching to the sides of the eye cup 1. This head band is preferably of resilient material and may have a buckle for adjusting it to the head size required.

The outer cup 1 is provided with a series of holes or openings 14 therethrough and the inner cup 5 is also provided with a plurality of holes or openings 15 therethrough. The holes 14 and the holes 15 are spaced in staggered relation with each other so that the air coming through the cup 1 will be deflected and have its direction changed before it goes through the opening 15 into the interior of the eye cup.

Figure 4:
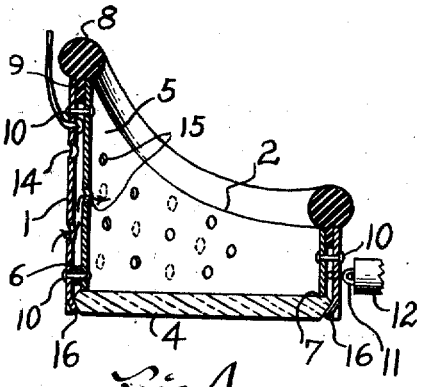
Fig. 4 is a cross section similar to Fig. 2 showing a modification of the invention.

In Fig. 4 is shown a modification wherein the lens 4 instead of being held by the flange 3 of the eye cup is held by a series of spring fingers 16 which may be bent or sprung back to allow the lens to be entered or removed.

Figure 2:
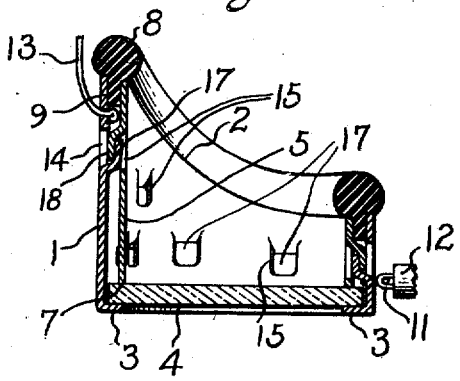
Fig. 2 is a cross section on line 2—2 of Fig. 1.
Figure 3:
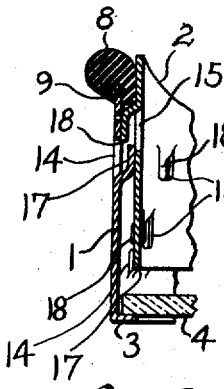
Fig. 3 is a partial cross section showing how the lens may be removed and replaced.

In Figs. 2 and 3 is shown an arrangement whereby the material in the eye cup 1 which has been displaced in making the opening 14 is bent back onto a flange 17 and the material which has been displaced in making the opening 15 in the eye cup 5 is bent out to form the flange 18. The flanges 17 and 18 overlie each other and provide a guide or slideway for sliding the inner cup 5 in the outer cup 1 for inserting or removing the lenses and they interlock each other when the inner eye cup 5 is pushed up to contact with the lens 4 to hold each other in place in spaced relation.

Figure 5:
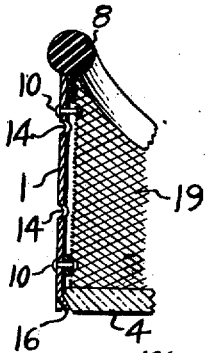
Fig. 5 is a partial cross section showing another modification.

In Fig. 5 the inner eye cup 5 has been replaced by a wire mesh screen cup 19, the construction being otherwise the same.

In Figs. 2, 4 and 5 the flange 9 of the rubber facing 8 is held between the inner and outer cups. In Fig. 3 wherein provision is made for sliding the inner cup within the outer cup the flange 9 of the facing 8 is secured to the cup 1 by rivets, cement or otherwise so that the inner cup may slide by the connection in its movement, but it will be seen that when the inner cup has been pushed in with its outer end connecting with the cup 4 the flange 9 will be between the two cups.

From the foregoing description it will be seen that the invention provides simple arrangements for holding the face contact member for ventilating the eye cup, for holding the lens, and for removing and replacing the lens, and that there is provided a simple, efficient and economical means for carrying out all the objects and advantages of the invention.

Having described my invention, I claim:

1. In a device of the character described, a pair of concentric annular eye cups spaced one within the other and separated one from the other, a flexible face engaging member having a portion extending between the two cups adjacent their inner ends, and means for securing the two cup together to grip and hold the portion of the face engaging member between the two cups in place therein.

2. In a device of the character described, a pair of concentric annular eye cups spaced one within the other and separated from each other, the said two cups having cut out lip portions bent to interengage each other to provide means whereby the inner cup may be slid longitudinally with respect to the outer cup and to provide ventilation through the cut out portions from which the lips were bent.

3. In a device of the character described, a pair of concentric annular eye cups spaced one within the other and separated from each other, and a flexible face engaging member having a portion held between the two cups adjacent their inner ends, the inner cup being shorter than the outer cup and adapted to seat a lens on the end thereof and the outer cup having lens engaging means adjacent its outer terminal portion to hold the lens in place in the inner cup.

4. In a device of the character described, a pair of concentric annular eye cups spaced one within the other and separated from each other, and a flexible face engaging member having a portion held between the two cups adjacent their inner ends, the inner cup being shorter than the outer cup and adapted to seat a lens on the outer end thereof and the outer cup having a lens engaging portions adjacent its outer end adapted to hold the lens in place on the inner cup, said inner and outer cups having ventilation openings therethrough.

5. In a device of the character described, a pair of eyecup members, one within the other, a resilient face contacting member having a face contacting portion and an attaching portion, means securing the attaching portion to one of the eyecup members and frictionally engaging clamping members which interlock and hold the eyecup members in related position one to the other and permit their separation without deformation or parts or connections.

6. In a device of the character described, a pair of eyecup members, one within the other, a resilient face contacting member having a face contacting portion and an attaching portion, means securing the attaching portion to one of the eyecup members, aligning means which align one eyecup with respect to the other and resiliently operable friction means which hold the two eyecups in aligned position and permit their separation one from the other without deformation of the parts or connections.

7. In a device of the character described, an outer eye cup member having its inner end shaped substantially to a face contacting contour and having an offset attaching portion extending therefrom, an inner eye cup member within the outer eye cup member and having its inner end shaped substantially to the same contour as the inner end of the outer eye cup member and having an offset attaching portion extending therefrom, a resilient face contacting member having a face contacting portion shaped to fit the contour of the face and an attaching portion extending therefrom, the inner end of said outer eye cup, the inner end of said inner eye cup and the attaching portion of the face contacting member overlying each other adjacent the face contacting portion of the face contacting member, and means securing the attaching portion of the face contacting member to one of said eye cup members, the offset attaching portions of the eye cup members engaging and interlocking with each other to hold the eye cup members in related aligned position one with the other without deformation of parts or connections.

8. In a device of the character described, an outer eye cup member having its inner end shaped substantially to a face contacting contour, an inner eye cup member within the outer eye cup member and having its inner end shaped substantially to the same contour as the inner end of the outer eye cup member, a resilient face contacting member having a face contacting portion shaped to the contour of the face and an attaching portion extending therefrom, the inner end of said outer eye cup, the inner end of the said inner eye cup and the attaching portion of the face contacting member overlying each other adjacent the face contacting portion of the face contacting member, means securing the attaching portion of the face contacting member to one of said eye cup members, and means for aligning and locking the eye cup members in related position one with the other without deformation of parts or connections.

In testimony whereof I have affixed my signature.

WILLIAM J. WRIGHTON.